United States Patent [19]

Bluthe et al.

[11] Patent Number: 4,978,801
[45] Date of Patent: Dec. 18, 1990

[54] PREPARATION OF AROMATIC ALDEHYDES

[75] Inventors: Norbert Bluthe, Villeurbanne; Robert Perron, Charly, both of France

[73] Assignee: Rhone-Poulenc Chimie, Courbevoie, France

[21] Appl. No.: 43,423

[22] Filed: Apr. 28, 1987

[30] Foreign Application Priority Data

Apr. 28, 1986 [FR] France .................................. 86 06364

[51] Int. Cl.$^5$ ............................................. C07C 45/49
[52] U.S. Cl. .................................... 568/428; 546/298; 568/429; 568/451; 568/454
[58] Field of Search ............... 568/428, 429, 451, 454, 568/429; 546/298

[56] References Cited

U.S. PATENT DOCUMENTS

| | | | |
|---|---|---|---|
| 3,960,932 | 6/1976 | Heck | 568/428 |
| 4,338,467 | 7/1982 | Takano et al. | 568/428 |
| 4,536,344 | 8/1985 | Fiedler et al. | 568/428 |
| 4,605,749 | 8/1986 | Buchmann et al. | 568/428 |
| 4,613,702 | 9/1986 | Leconte | 568/428 |

FOREIGN PATENT DOCUMENTS

| | | | |
|---|---|---|---|
| 0034430 | 8/1981 | European Pat. Off. | 568/428 |
| 2364039 | 7/1974 | Fed. Rep. of Germany | 568/428 |
| 3242582 | 5/1984 | Fed. Rep. of Germany | 568/428 |
| 0164736 | 9/1984 | Japan | 568/428 |

Primary Examiner—Werren B. Lone
Attorney, Agent, or Firm—Burns, Doane Swecker & Mathis

[57] ABSTRACT

Aromatic aldehydes are more efficiently produced by reacting carbon monoxide/hydrogen admixture with an aromatic halide in the presence of a noble metal-based catalyst, a tertiary nitrogenous based and, if necessary, a noble metal complexing agent, e.g., a phosphine or phosphite, wherein the $CO/H_2$ ratio is less than 1.

19 Claims, No Drawings

PREPARATION OF AROMATIC ALDEHYDES

CROSS-REFERENCE TO RELATED APPLICATION

Our copending application Ser. No. 043,363, filed concurrently herewith and assigned to the assignee hereof, now U.S. Pat. No. 4,942,240.

BACKGROUND OF THE INVENTION

1. Field of the Invention

The present invention relates to the preparation of aromatic aldehydes, and, more especially, to the preparation of aromatic aldehydes by the hydrocarbonylation of aromatic halides in the presence of a noble metal, a tertiary nitrogenous base and, where necessary, a phosphorus compound.

2. Description of the Prior Art

A process for the preparation of aldehydes by reacting a gaseous mixture of hydrogen and carbon monoxide with an organic halide of the group consisting of aromatic, vinyl and heterocyclic halides in the presence of a tertiary amine and a palladium catalyst which consists of a complex of a divalent palladium derivative with a phosphine (triphenylphosphine), a phosphite or an arsine, or of the combination of a divalent palladium salt (acetate or chloride) or finely divided palladium metal with a phosphine, phosphite or arsine complexing agent, is described in U.S. Pat. No. 3,960,932. In the latter case, the ratio of the number of g-at. of P to the number of g-at. of Pd may be between 0.5 and 5. The reaction is carried out at a temperature of 75° C. to 175° C. and at a pressure of 7 to 140 bar. In general, the nitrogenous base is used in slight excess compared with the theoretical amount required for the neutralization of the hydracid which is a byproduct of the reaction. This process is particularly well suited for the preparation of aromatic aldehydes by the hydrocarbonylation of the corresponding bromides. In spite of the good results obtained, this process suffers from a serious disadvantage in the time periods required for reaction, i.e., periods on the order of 10 to 26 hours. These reaction times result in low productivities of the equipment and negate any industrial value of the process.

In order to alleviate the disadvantages of the process described in U.S. Pat. No. 3,960,932, the hydrocarbonylation of aromatic halides at pressures of 20 to 400 bar, at a temperature of 80° to 250° C., in the presence of a noble metal-based catalyst, a tertiary nitrogenous base and a large amount of a phosphine or a phosphite has been proposed. See published European Patent Application No. 0,109,606. The amount of the phosphorus derivative represents from 2 to $10^5$ times the molar amount of the catalyst, preferably from 10 to 1000 times. As it enables the use of high reaction temperatures without degradation of the catalyst, this particular process enables the reaction rate, and, consequently, the productivity of the equipment to be increased. However, the increase in the reaction rate is still considered insufficient and inexorably linked to the use of high temperatures.

In the processes of the prior art, the highest possible pressures have been used (in the '606 European application, it is noted that the total pressure must be at least 20 bar) and the $CO/H_2$ ratio in the gaseous mixture has not been considered critical; this ratio is preferably equal to 1.

Cf. Schoenberg et al, *Journal American Chemical Society*. 96, No. 25, pp. 7761-7764 (Dec. 11, 1974); EP-A-No. 0,165,881.

SUMMARY OF THE INVENTION

Accordingly, a major object of the present invention is the provision of an improved process for the more efficient preparation of aromatic aldehydes. Indeed, from thorough consideration and detailed analysis of the totality of the reaction parameters, it has now unexpectedly been determined that the $CO/H_2$ ratio has a marked effect on the reaction rate.

Briefly, the present invention features a process for preparing aromatic aldehydes by reacting a carbon monoxide/hydrogen admixture with an aromatic halide, namely, bromide or iodide, in the presence of a noble metal-based catalyst, a nitrogenous base and, if required, a noble metal complexing agent selected from among the phosphines and phosphites, wherein the $CO/H_2$ volumetric ratio is less than 1.

DETAILED DESCRIPTION OF THE PREFERRED EMBODIMENTS OF THE INVENTION

More particularly according to the present invention, it has now surprisingly been determined that, at a given total pressure, the reaction rate increases with decreasing partial pressure of carbon monoxide and that, at a specific carbon monoxide pressure, the reaction rate increases with the pressure of hydrogen. It has additionally been determined that judicious selection of the $CO/H_2$ ratio enables the reaction to be carried out at an excellent rate at relatively low total pressures, for example, less than 20 bar. Finally, the higher the concentration of the base in the reaction medium, the greater is the effect of decreasing the partial pressure of carbon monoxide on the reaction rate. This constitutes another object of the present invention. The $CO/H_2$ ratio is preferably less than or equal to 0.9 and, even more preferably, is less than or equal to 0.8.

The total pressure of the gaseous mixture may vary over wide limits, including those of the prior art. More specifically, the total pressure may range from 1 to 250 bar and preferably from 10 to 150 bar. However, the total pressure depends, to a certain extent, on the partial pressures of carbon monoxide and hydrogen. In fact, as mentioned above, the reaction rate increases with decreasing partial pressure of CO. From this point of view, it is generally preferable to carry out the reaction at CO partial pressures less than or equal to 20 bar and preferably less than or equal to 15 bar. The lower limit for the pressure of CO is that above which, under the conditions of the reaction, the rate at which carbon monoxide changes from the gaseous phase to the liquid phase becomes less than the rate of the reaction of the carbon monoxide with the aromatic halide. The partial pressure of carbon monoxide may be as low as 0.5 bar. It preferably ranges from 1 to 20 bar. Although the reaction rate increases with the partial pressure of hydrogen, it is not desirable to exceed values above which secondary reactions, such as hydrogenolysis of bromine or iodine, are favored at the expense of the hydrocarbonylation reaction. The partial pressure of hydrogen must therefore be selected such as to ensure, considering the other reaction conditions, the highest possible reaction rate, as well as the highest possible selectivity. In general, it is not necessary to use a partial pressure of hydrogen greater than 100 bar. The lower limit for the partial pressure of hydrogen depends on the value selected for the partial pressure of the carbon monoxide. Typically, the partial pressure of hydrogen may be as low as 2 bar, preferably 5 bar. Under these conditions, the total reaction pressure depends on the selected partial pressures of CO and $H_2$.

As discussed above, the effect of the partial pressures of CO and $H_2$ on the reaction rate becomes more apparent with increasing concentration of the tertiary nitrogenous base. It is preferable that the concentration of the nitrogenous base, expressed as moles per liter of the mixture of the aromatic halide, the base and, where appropriate, the solvent, is maintained during the reaction period at a value not less than 2 and, preferably, not less than 2.5.

The various other reaction conditions are those described in the prior art, e.g., the '932 patent and the '606 patent application noted above.

To carry out the process according to the invention, a finely divided noble metal of Group VIII of the Periodic Table of elements, such as palladium, rhodium or iridium, or their inorganic or organic acid salts or their complexes with electronic pair donor compounds, especially their complexes with phosphines, phosphites or arsines, are advantageously used as catalysts. Palladium derivatives are particularly well suited for implementing the process according to the invention. As specific examples of such palladium derivatives, representative are palladium (II) carboxylates (acetate, propionate, butyrate and benzoate), palladous chloride and palladium complexes of the general formulae $PdX_2[P(R)_3]_2$ or $PdX_2[P(OR)_3]_2$, in which X represents a halogen (bromine, chlorine) atom or an inorganic or carboxylic acid residue and R represents a hydrocarbon radical. Dichlorodi(triphenylphosphino)palladium (II) and dibromodi(tritolylphosphino)palladium (II) are especially noteworthy.

The amount of catalyst, expressed as gram-atoms of metal or as moles of metal derivative per mole of aromatic halide, may vary over wide limits. Thus, it may range from $10^{-5}$ to $10^{-1}$ g-at or moles per mole, and preferably from $10^{-4}$ to $10^{-2}$ g-at or moles per mole.

Exemplary of the tertiary nitrogenous base, amines of the following general formula are representative:

$$N(R_1)_3$$

in which the $R_1$ radicals, which may be identical or different, represent hydrocarbon radicals containing from 1 to 20 carbon atoms, such as alkyl, cycloalkyl or aryl radicals. The symbols $R_1$ are preferably alkyl radicals containing from 1 to 10 carbon atoms or cycloalkyl radicals containing from 5 to 10 carbon atoms. Triethylamine, tri-n-propylamine, tri-n-butylamine, methyldibutylamine, methyldicyclohexylamine and ethyldiisopropylamine are specific examples of such bases. Heterocyclic tertiary amine bases such as pyridine and picolines may also be used.

The amount of base must be sufficient both for neutralizing the hydracid released by the reaction and such that the base concentration is at least 2 mols per liter of the reaction mixture throughout the reaction period. When these two conditions are satisfied, there is no critical upper limit for the amount of the base, which can be used in a large excess compared with that amount theoretically required for the neutralization of the hydracid formed. In order to maintain the concentration of the base at least equal to the limiting values given above throughout the period of the reaction, the amount of base must be calculated such that, upon completion of the reaction, the concentration of the base is at least equal to these values. An additional amount of base may also be added as the reaction proceeds, such as to compensate for that amount consumed by the neutralization of the hydracid.

The phosphines and phosphites which are suitable for carrying out the subject reaction are those noted in the U.S. Pat. No. 3,960,932 or in European Patent Application No. 0,109,606, hereby incorporated by reference. Exemplary of these compounds, representative are: triphenylphosphine, triphenylphosphite, diethylphenylphosphine, diethylphenylphosphite, tritolylphosphine, tritolylphosphite, trinaphthylphosphine, trinaphthylphosphite, diphenylmethylphosphine, diphenylmethylphosphite, diphenylbutylphosphine, diphenylbutylphosphite, tris(p-methoxycarbonylphenyl)phosphine, tris(p-methoxycarbonylphenyl)phosphite, tris(p-cyanophenyl)-phosphine, tris(cyanophenyl)phosphite, triethylphosphite, tributylphosphine and tributylphosphite.

The presence of a free phosphorus-containing complexing agent in the reaction medium depends on the nature of the catalyst and/or the reaction conditions. When the catalyst is a complex of a noble metal with a phosphine or a phosphite, the presence of the latter in free state is not indispensable. However, it proves advantageous when the reaction is carried out at a high temperature, for example at a temperature greater than 150° C. When a noble metal is employed in the metallic state or as a derivative which is not complexed with a phosphine or a phosphite, such as, for example, noble metal carboxylates, it is essential to carry out the reaction in the presence of the phosphorus-containing compound. When the reaction is carried out in the presence of a phosphite or a phosphine, the amount thereof is selected such that the ratio of the number of gram-atoms of phosphorus (P) to the number of gram-atoms of metal (M) is at least equal to 2. The ratio P/M may have values as high as 10,000. A P/M ratio of from 5 to 1,000 is typically suitable.

The process according to the invention is particularly well suited for the preparation of aromatic aldehydes having the general formula:

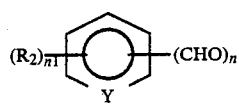

(I)

in which:

n is 1 or 2;

$n_1$ is an integer of from 1 to 4; and $R_2$ represents: a hydrogen, fluorine or chlorine atom; an alkyl radical which may be substituted, if required, with one or more chlorine and/or fluorine atoms; cycloalkyl; aryl; alkoxy; cycloalkoxy; aryloxy; alkoxycarbonyl; cycloalkoxycarbonyl; aryloxycarbonyl; alkyl-, cycloalkyl- or arylcarbonyloxy radical, optionally substituted with one or more fluorine and/or chlorine atoms; a nitrile group; or, when $n_1$ is equal to 2, two $R_2$ radicals borne by neighboring carbon atoms which form a hydrocarbon ring or a heterocycle with the latter.

When $n_1$ is greater than 1, the different substituents $R_2$ may be identical or different.

Y represents a divalent radical —CH— or a nitrogen atom.

In the formula (I), $R_2$ preferably represents:

(i) straight or branched chain alkyl radicals containing from 1 to 20 carbon atoms, such as methyl, ethyl, propyl, butyl, pentyl, 2-ethylhexyl, trifluoromethyl, difluorochloromethyl, trichloromethyl and decyl radicals. $R_2$ more preferably represents a lower alkyl radical (containing from 1 to 4 carbon atoms);

(ii) cycloalkyl radicals containing from 5 to 10 carbon atoms, such as cyclopentyl, cyclohexyl and cyclooctyl;

(iii) phenyl radicals which may be substituted, if required, with one or more lower alkyl or lower alkoxy radicals, such as phenyl, xylyl, tolyl, methoxyphenyl and ethoxyphenyl;

(iv) alkoxy radicals containing from 1 to 20 carbon atoms, preferably from 1 to 10 carbon atoms, such as methoxy, ethoxy, isopropyloxy, butoxy, trifluoromethoxy, difluorochloromethoxy and trichloromethoxy;

(v) alkoxycarbonyl radicals containing from 1 to 10 carbon atoms in the alkoxy residue, preferably lower alkoxycarbonyl radicals such as methoxy-, ethoxy-, isopropyloxy- and butyloxycarbonyl;

(vi) cycloalkoxycarbonyl radicals containing from 5 to 10 carbon atoms, such as cyclopentyloxycarbonyl and cyclohexyloxycarbonyl;

(vii) phenyloxycarbonyl and tolyloxycarbonyl radicals;

(viii) alkylcarbonyloxy radicals containing from 1 to 10 carbon atoms, such as acetoxy, propionyloxy and butyroyloxyl;

(ix) cycloalkylcarbonyloxy radicals containing from 5 to 10 carbon atoms, such as cyclopentanoyloxy and cyclohexanoyloxy;

(x) benzoyloxy, methylbenzoyloxy and dimethylbenzoyloxy radicals; and (xi) when two $R_2$ radicals form a ring together with the neighboring carbon atoms from which they depend, this ring may more particularly be a benzene ring which may be substituted, if required, with lower alkyl or alkoxy radicals, or a methylenedioxy ring (1,3-dioxacyclopentane).

As specific examples of aldehydes of the formula (I) which may be prepared by the process of the invention, representative are: benzaldehyde, tolualdehydes, anisaldehydes, vanillin, trimethoxybenzaldehyde, 3,4-methylenedioxybenzaldehyde (piperonal), terephthaldehyde, o-, m- or p-trifluoromethoxybenzaldehydes, o-, m- or p-trichloromethoxybenzaldehydes, o-, m- or p-difluorochloromethoxybenzaldehydes, naphthylaldehydes and formylpyridines.

Exemplary of the aromatic halide starting materials used in the process according to the invention, compounds having the following general formula are illustrative:

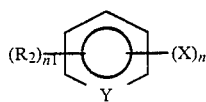

(II)

in which n, $n_1$, $R_2$ and Y are as defined above and X represents a bromine or iodine atom. As specific examples of such compounds, representative are: bromobenzene, o-, m- and p-bromotoluenes, 2,3-dimethylbromobenzene, 2,4-dimethylbromobenzene, o-, m- and p-trifluorobenzenes, o, m- and p-fluoroiodobenzenes, 2,3-difluorobromobenzene, o, m- and p-trifluoromethylbromobenzenes, o-, m- and p-trifluoromethyliodobenzenes, trifluoromethoxybromobenzenes, trifluoromethoxyiodobenzenes, o-, m- and p-difluorochloromethylbenzenes, difluorochloromethoxybromobenzenes, bromobenzonitriles, dibromobenzenes, 1-bromonaphthalene, 2-bromopyridine, 4-bromopyridine, p-bromodiphenylether, methyl bromobenzoates, p-bromoanisole, orthobromoanisole, p-bromodiphenylether, methyl bromobenzoates, p-bromoanisole, orthobromoanisole, p-bromophenetole, 3,4-dimethoxybromobenzene, 3,4,5-trimethoxybromobenzene and 3-bromomethylenedioxybenzene.

The temperature at which the process according to the invention is carried out may vary over wide limits. In general, any temperature within the range of from 50° to 250° C. may be used. The temperature preferably ranges from 75° to 200° C.

The total pressure of the hydrogen/carbon monoxide mixture advantageously ranges from 1 to 400 bar and preferably from 10 to 250 bar. The $H_2/CO$ volume ratio may also vary over wide limits. In general, it ranges from 0.1 to 10, and preferably from 0.2 to 5.

The process according to the present invention is carried out in liquid phase. Where appropriate, a solvent which is inert under the conditions of the reaction is used. For this purpose, saturated aliphatic or cycloaliphatic hydrocarbons (hexane, cyclohexane) or aromatic hydrocarbons: benzene, toluene, xylene; esters such as methyl benzoate, methyl terephthalate, methyl adipate, dubutyl phthalate, esters or ethers of polyhydric alcohols such as tetraethyleneglycol diacetate, cyclic ethers (tetrahydrofuran and dioxane) may be used.

From a practical point of view, the process of the invention is carried out simply by introducing the aryl halide, the nitrogenous base, the catalyst and, where appropriate, the phosphorus derivative and a solvent into an inert autoclave and then supplying a $CO/H_2$ mixture into the closed autoclave at a sufficient pressure. The contents of the autoclave are then heated to the appropriate temperature, under stirring, until the absorption of gases ceases. The pressure in the autoclave may be maintained constant during the period of the reaction by connecting it to a reservoir of gaseous mixture at the chosen pressure. Upon completion of the reaction, the contents of the autoclave are cooled, the autoclave is degassed and the reaction mass is filtered to separate the hydrohalide of the nitrogenous base. The filtrate is then distilled in order to separate the organic constituents of the reaction medium. The distillation residue which contains the catalyst may be recycled for use in a new operation.

The process according to the invention may be carried out batchwise or continuously.

In order to further illustrate the present invention and the advantages thereof, the following specific examples are given, it being understood that same are intended only as illustrative and in nowise limitative.

In said examples to follow, the reaction rate is expressed either as the number of millimoles of gas absorbed per hour (mmol.h$^{-1}$), or as the number of bar of gas absorbed per hour (bar.h$^{-1}$). As the reaction rate is of the zero order with respect to the aromatic halide, and therefore independent of the substrate concentration in the reaction medium the hydrocarbonylation was not carried out to its completion; since the reaction occurs essentially at the same rate throughout its course, it was sufficient to determine such rate after a limited time of contact of the reagents.

EXAMPLE 1

A pressure-resistant stainless steel reactor (trademark HASTELLOY B2) equipped with a heating device and stirred with a CAVITATOR type of stirrer was charged with:

(i) 74 g (368 mmoles) of 3,4-bromomethylenedioxybenzene;
(ii) 40 mg (0.179 mmole) of palladium diacetate;
(iii) 3.77 g (14.4 mmoles) of triphenylphosphine;
(iv) 64 ml of toluene;
(v) 18 ml of dibutyl phthalate; and
(vi) 80 g (792 mmoles) of triethylamine (100 ml), i.e., a concentration of 3.35 moles/l.

The reactor was then closed and purged with a gaseous mixture comprising 1 volume of CO for 3 volumes of hydrogen. This mixture was charged to a pressure of 4 bar and the contents of the reactor were heated to 170° C., and the pressure was then adjusted to 30 bar using the same mixture.

The pressure in the reactor was maintained constant by supplying the reactor with an equivolume mixture of CO and $H_2$. The pressure drop in the reservoir was monitored. After 2 h, 30 min, of reaction, the supply of the gaseous mixture was discontinued and the contents of the reactor were cooled. Analysis of the gases in the air space of the reactor (the gaseous phase above the liquid phase) by gas chromatography evidenced that the $CO/H_2$ ratio was equal to ⅓.

Taking into account the pressure drop recorded in the reservoir during the period of the experiment, the initial reaction rate was 64 $bar.h^{-1}$.

COMPARATIVE EXAMPLE

The preceding experiment was repeated using a $CO/H_2$ ratio of 1, the total pressure being 30 bar.

The initial reaction rate, expressed as $bar.h^{-1}$, was 44.

A comparison of this example with Example 1 demonstrates that, all other conditions being equal, the reaction rate increased when the $CO/H_2$ ratio was changed from 1 to ⅓.

EXAMPLE 2

Example 1 was repeated using a $CO/H_2$ ratio of 3/17.
Under these conditions, the initial reaction rate was 88 $bar.h^{-1}$.

EXAMPLE 3

A 125 ml stainless steel autoclave (trademark HASTELLOY B2) were charged with:

(i) 20.1 g (100 mmol) of 3,4-bromoethylenedioxybenzene;
(ii) 11.2 mg (0.05 mmol) of palladium diacetate;
(iii) 1.05 g (4 mmol) of triphenylphosphine;
(iv) 20 ml of a toluene/dibutylphthalate mixture in a volume ratio of 3/1; and
(v) 22.26 g (220 mmol) of triethylamine (31 ml), i.e., a concentration of 3.49 moles/l.

2 bar of carbon monoxide followed by 7 bar of hydrogen were then introduced. The contents of the reactor, agitated by a reciprocating shaking system, were heated to 170° C. and then connected to a reservoir containing a 1/1 mixture of carbon monoxide/hydrogen, the pressure drop in which made it possible to monitor the progress of the reaction. The pressure in the autoclave was maintained at 15 bar during the period of the experiment. These conditions were maintained for 4 hours. The contents of the autoclave were degassed. The initial rate of absorption of the $CO/H_2$ mixture rose to 47 $mmoles.h^{-1}$. 7.56 g of piperonal were formed and the conversion rate of bromomethylenedioxybenzene rose to 56%.

EXAMPLE 4

The reaction was carried out as in Example 3, but under a CO partial pressure of 1 bar and an $H_2$ partial pressure of 8 bar. The experiment was stopped after 2 hours under these conditions.

The initial rate of absorption of the $CO/H_2$ mixture rose to 67 $mmol.h^{-1}$. 5.94 g of piperonal were formed for a bromomethylenedioxybenzene conversion rate of 44%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an aromatic aldehyde, comprising reacting carbon monoxide/hydrogen admixture with an aromatic halide in the presence of a noble metal-based catalyst and a tertiary nitrogenous base, and wherein the $CO/H_2$ ratio is less than 1.

2. The process as defined by claim 1, the reaction mixture further comprising a phosphine or phosphite noble metal complexing agent.

3. The process as defined by claims 1 or 2, said aromatic halide comprising an aromatic bromide or iodide.

4. The process as defined by claim 3, wherein the $CO/H_2$ ratio is no greater than 0.9.

5. The process as defined by claim 4, wherein the $CO/H_2$ ratio is no greater than 0.8.

6. The process as defined by claim 3, wherein the total reaction pressure ranges from 1 to 250 bar.

7. The process as defined by claim 6, wherein the pressure of carbon monoxide is no greater than 20 bar.

8. The process as defined by claim 3, wherein the concentration of said tertiary nitrogenous base, expressed in moles per liter of reaction mixture, is maintained at a value of at least two moles/liter throughout the reaction period.

9. The process as defined by claim 3, for the preparation of an aromatic aldehyde of the following general formula:

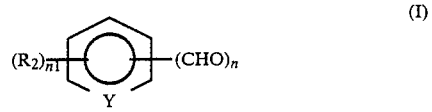

in which n is 1 or 2; $n_1$ is an integer of from 1 to 4; $R_2$ is a hydrogen, fluorine or chlorine atom, an alkyl radical, an alkyl radical bearing at least one chlorine and/or fluorine atom substituent, a cycloalkyl, aryl, alkoxy, cycloalkoxy, aryloxy, alkoxycarbonyl, cycloalkoxycarbonyl, aryloxycarbonyl, alkyl-, cycloalkyl- or arylcarbonyloxy radical, or a substituted such radical bearing at least one fluorine and/or chlorine atom substituent, a nitrile radical, or, when $n_1$ is equal to 2, two $R_2$ radicals borne by adjacent carbon atoms may together form a hydrocarbon ring or a heterocycle therewith; and Y is a divalent radical —CH— or a nitrogen atom; comprising reacting carbon monoxide/hydrogen admixture with an aryl halide of the general formula:

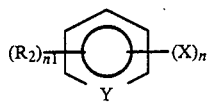
(II)

in which n, $n_1$, $R_2$ and Y are as defined above and X is a bromine or iodine atom.

10. The process as defined by claim 9, wherein the tertiary nitrogenous base is a tertiary amine.

11. The process as defined by claim 9, carried out at a temperature of from 50° to 250° C.

12. The process as defined by claim 9, wherein the catalyst comprises palladium metal or a palladium compound.

13. The process as defined by claim 12, wherein the amount of palladium, expressed as gram-atoms of noble metal or as moles of metal compound per mole of aromatic halide, ranges from $10^{-5}$ to $10^{-1}$.

14. The process as defined by claim 2, wherein the amount of phosphine or phosphite is such that the ratio of the number of gram-atoms of phosphorus therein to the number of gram-atoms of metal ranges from 1 to 10,000.

15. The process as defined by claim 9, wherein the catalyst comprises a Group VIII noble metal.

16. The process as defined by claim 9, carried out in an inert organic solvent.

17. The process as defined by claim 1, wherein the catalyst comprises a complex of a noble metal with a phosphine or phosphite.

18. The process as defined by claim 1, wherein the initial reaction rate measured as absorption of said $CO/H_2$ equals at least 64 bar/hour.

19. The process as defined by claim 1, wherein the initial reaction rate measured as absorption of said $CO/H_2$ equals at least 47 millimoles/ hour.

* * * * *